United States Patent
Gazenko

(10) Patent No.: US 7,524,623 B2
(45) Date of Patent: Apr. 28, 2009

(54) METHOD AND DEVICE FOR RAPID DETECTION OF MICROORGANISMS BY CHANGING THE SHAPE OF MICRO-COLONIES

(75) Inventor: Sergey Gazenko, Cincinnati, OH (US)

(73) Assignee: Nanologix, Inc., Hubbard, OH (US)

( * ) Notice: Subject to any disclaimer, the term of this patent is extended or adjusted under 35 U.S.C. 154(b) by 234 days.

(21) Appl. No.: 11/393,012

(22) Filed: Mar. 30, 2006

(65) Prior Publication Data

US 2007/0238139 A1 Oct. 11, 2007

Related U.S. Application Data

(63) Continuation-in-part of application No. 10/628,110, filed on Jul. 28, 2003, now abandoned.

(51) Int. Cl.
*C12Q 1/00* (2006.01)
*C12Q 1/02* (2006.01)
*C12N 11/00* (2006.01)

(52) U.S. Cl. ................. 435/4; 435/29; 435/174

(58) Field of Classification Search .................. None
See application file for complete search history.

(56) References Cited

U.S. PATENT DOCUMENTS

| | | | |
|---|---|---|---|
| 3,911,140 A | 10/1975 | Osborne et al. | |
| 5,449,617 A | 9/1995 | Falkenberg et al. | |
| 5,624,815 A | 4/1997 | Grant et al. | |
| 5,650,323 A | 7/1997 | Root | |
| 5,660,990 A | 8/1997 | Rao et al. | |
| 5,716,798 A | 2/1998 | Monthony et al. | |
| 5,770,440 A | 6/1998 | Berndt | |
| 6,043,027 A | 3/2000 | Selick et al. | |
| 6,372,183 B1 | 4/2002 | Akong et al. | |
| 6,377,721 B1 | 4/2002 | Walt et al. | |
| 6,696,286 B1 | 2/2004 | Halverson et al. | |
| 6,716,629 B2 | 4/2004 | Hess et al. | |
| 6,729,352 B2 | 5/2004 | O'Connor et al. | |
| 6,743,581 B1 | 6/2004 | Vo-Dinh | |
| 6,767,706 B2 | 7/2004 | Quake et al. | |
| 6,818,435 B2 * | 11/2004 | Carvalho et al. | 435/286.5 |
| 6,852,222 B2 | 2/2005 | Clark et al. | |
| 7,125,674 B2 | 10/2006 | Beattie | |
| 7,338,773 B2 | 3/2008 | Goldbard et al. | |
| 2002/0153046 A1 | 10/2002 | Dantsker et al. | |
| 2002/0189374 A1 | 12/2002 | DeSilets et al. | |
| 2003/0096268 A1 | 5/2003 | Weiner et al. | |
| 2004/0146965 A1 | 7/2004 | Brayton | |

OTHER PUBLICATIONS

Martin et al. Generation of Larger Numbers of Separated Microbial Populations by Cultivation in Segmented-Flow Microdevices; Lab on a Chip, vol. 3 (2003) pp. 202-207.*
Walker et al. Insect Cell Culture in Microfluidic Channels; Biomedical Microdevices, vol. 4, No. 3 (2002) pp. 161-166.*
Thiébaud et al. PDMS Device for Patterned Application of Microfluids to Neuronal Cells Arranged by Microcontact Printing; Biosensors and Bioelectronics, 17 (2002) pp. 87-93*
Moorthy et al. In Situ Fabricated Porous Filters for Microsystems; Lab on a Chip, vol. 3 (2003) pp. 62-66.*
Yang et al. Cell Docking and On-Chip Monitoring of Cellular Reactions with a Controlled Concentration Gradient on a Microfluidic Device; Analytical Chemistry, vol. 74, (2002) pp. 3991-4001.*
BioTK - Projects partnering - Project details, To Change the face of modem microbiological diagnostics, PHARM techexpo, www.biotk. com/partnering_details.php?id=15, Jul. 24, 2004, printed Nov. 25, 2008.
Ford, Vanessa, Office Action for U.S. Appl. No. 10/141,677 entitled "Micromethod and device for rapid detection, enumeration and identification of entitles," Aug. 20, 2008 (9).
Ford, Vanessa, Office Action for U.S. Appl. No. 10/141,677 entitled "Micromethod and device for rapid detection, enumeration and identification of entitles," Nov. 29, 2007 (8).

(Continued)

*Primary Examiner*—Jon P Weber
*Assistant Examiner*—Paul C. Martin
(74) *Attorney, Agent, or Firm*—Eckert Seamans Cherin & Mellott, LLC; Carol A. Marmo

(57) ABSTRACT

This invention describes a method of rapid detection of micro-colonies of microorganisms by changing their shape from a regular semi-sphere to a long and thin cylinder. Cells are trapped by filtration in long (diameter/length=1/10-1/100), cylindrical, parallel, micro-channels that are open from both sides, and attached to a filter from one side. A micro-channel plate houses a multiplicity of micro-channels (diameter of each channel=1 -20 μm, and length 100-1000 μm). The micro-channel plate with cells trapped on the surface of the filter is attached to a nutrient media agar block. Cells produce micro-colonies of a long and thin shape according the shape of the micro-channel. The growth of microorganisms in the micro-channels permits a change in the number of cells to accomplish light absorbance. Fewer cells need a shorter time to reproduce. Thus detection and counting of cells can be accomplished in a rapid fashion. The light absorbance can be enhanced by additional coloration of micro-colonies by cell dyes or artificial chromogenic or fluorogenic substrates.

20 Claims, 6 Drawing Sheets

OTHER PUBLICATIONS

Ford, Vanessa, Office Action for U.S. Appl. No. 10/141,677 entitled "Micromethod and device for rapid detection, enumeration and identification of entitles," Jun. 14, 2007 (7).

Ford, Vanessa, Office Action for U.S. Appl. No. 10/141,677 entitled "Micromethod and device for rapid detection, enumeration and identification of entitles," Feb. 8, 2007 (6).

Ford, Vanessa, Advisory Action for U.S. Appl. No. 10/141,677 entitled "Micromethod and device for rapid detection, enumeration and identification of entitles," Jun. 1, 2006 (4a).

Ford, Vanessa, Office Action for U.S. Appl. No. 10/141,677 entitled "Micromethod and device for rapid detection, enumeration and identification of entitles," Jul. 27, 2005 (4).

Ford, Vanessa, Office Action for U.S. Appl. No. 10/141,677 entitled "Micromethod and device for rapid detection, enumeration and identification of entitles," Sep. 8, 2004 (3).

Ford, Vanessa, Office Action for U.S. Appl. No. 10/141,677 entitled "Micromethod and device for rapid detection, enumeration and identification of entitles," Dec. 12, 2003 (2).

Ford, Vanessa, Office Action for U.S. Appl. No. 10/141,677 entitled "Micromethod and device for rapid detection, enumeration and identification of entitles," May 30, 2003 (1).

Diramio, Jacqueline A., Office Action for U.S. Appl. No. 11/109,857 entitled "Device for rapid detection and identification of single microorganisms without preliminary growth," Sep. 24, 2008 (4).

Diramio, Jacqueline A, Office Action for U.S. Appl. No. 11/109,857 entitled "Device for rapid detection and identification of single microorganisms without preliminary growth," May 21, 2008 (3).

Diramio, Jacqueline A, Advisory Action for U.S. Appl. No. 11/109,857 entitled "Device for rapid detection and identification of single microorganisms without preliminary growth," Feb. 5, 2008 (2a).

Diramio, Jacqueline A, Office Action for U.S. Appl. No. 11/109,857 entitled "Device for rapid detection and identification of single microorganisms without preliminary growth," Nov. 13, 2007 (2).

Diramio, Jacqueline A, Office Action for U.S. Appl. No. 11/109,857 entitled "Device for rapid detection and identification of single microorganisms without preliminary growth," May 29, 2007 (1).

* cited by examiner

Enlarged picture of micro channels with trapped cell and micro colony formation.

Micro-channels with micro colonies: (A) non colored micro colonies; (B) colored by chromogenic substrates or dyes; (C) colored by fluorogenic substrates or dyes.

METHOD AND DEVICE FOR RAPID DETECTION OF MICROORGANISMS BY CHANGING THE SHAPE OF MICRO-COLONIES

CROSS REFERENCE TO RELATED APPLICATION

This application is a continuation-in-part and claims priority to U.S. patent application Ser. No. 10/628,110, filed Jul. 28, 2003, and entitled "Method for Rapid Detection of Microorganisms by Changing the Shape of Micro Colonies."

FIELD OF THE INVENTION

The present invention relates generally to a method and apparatus for detecting microorganisms. More particularly, the present invention relates to a method and apparatus for rapidly detecting microorganisms during their preliminary growth on or in nutrient media. The invention utilizes one or a multiplicity of long, extremely small micro-channels having a diameter to length ratio between about 1/10 to 1/100 and a volume of about 1-500 picoliters. The apparatus and method function with or without fluorescent aids.

BACKGROUND OF THE INVENTION

Growing microorganisms in order to detect, enumerate and identify viable cells—bacteria, fungi, actinomycetes—is one of the most widely used procedures in microbiology. The ability to form a colony on or in an appropriate nutrient media is recognized as the most reliable criteria for cell viability. Formation of a colony requires different biochemical reactions and processes like respiration, transportation, synthesis and decomposing of different proteins, carbohydrates, lipids, enzymes, nucleic acids and many other substances, and creation of inner structures in order to finally reach cell reproduction and creation of a colony. The detection of live cells cannot be fully substituted by the simple detection of enzymes (enzymatic methods of detection), purified DNA or RNA (PCR methods), antigen—antibody interactions (Enzyme Immunological Analysis, ELISA, Immunoprecipitation, Immunofluorescence, Phagodiagnostics and others), fatty acids analysis (Chromatography), FTIR spectroscopy or other methods. This is due to the presence of specific molecules or even some working systems of the cell, which can be found in dead cells, cells under deadly stress, or cells without access to some required substances that are therefore restricted in growth potential.

Growth of microorganisms takes from hours to several days, or even weeks to form well visible colonies or a visible suspension of cells. The growth occurs either on artificial or natural nutrient media in solid or liquid form. There is a multitude of different media with selective criteria required for growth and total count of groups or species of microorganisms. These include media for growth, detection and enumeration of total number of bacteria (Tryptic Soy Agar and other), fungi, molds (Sabouraud Dextrose Agar, Potato Dextrose Agar and other), selective media for group of microorganisms like Gram-negative bacteria (MacConkey Agar, Levine EMB Agar and other), *Lactobacillius* (Lactobacillii MRS Agar) or *Salmonella* (SS Agar), certain microbes like *E. coli* O:157 (Sorbitol MacConkey Agar), *Vibrio chelerae* (TCBS Agar), *Campylobacter* (Triple Sugar Iron Agar) and many others. Growing periods on nutrient media is the most time consuming process in modern microbiological diagnostics. Reducing the time between the inoculation and detection of microorganisms is very important for rapid decisions in quality and process control in a multitude of industries including food, biotechnological, pharmaceutical, water treating industry, and also in medical microbiological diagnostics, environmental and biodefense control and monitoring, and scientific research. Thus, for example, significantly decreasing the time of microbiological analysis together with saving the high level of reliability (i.e., detection by growth—forming of colonies) is very important for modern medical diagnostics for early diagnostics of humans or animals infections, epidemiology, and detection of antibiotic resistant microbes and so on. Rapid analysis (analysis significantly faster than regular growth and further analysis) is also needed in food, pharmaceutical, and biotechnological industries for control and prevention of contamination in food, drugs, and medical devices and for environmental monitoring.

The term "colony" or "micro colony" in microbiology means a group of cells appearing from one single cell and consisting only from descendants of that cell. A colony or micro colony can have different shapes: semi-sphere if grown on the surface of solid agar, oval, cone or "star" if grown in solid or semi-solid agar, a dense or diffuse cloud if grown on semi-liquid or liquid media, or flat fibers growing from one center (fungi, actinomycetes, or some bacterial micro colonies).

There are several different methods and instruments employed to enhance colony visibility. The addition of special, non-toxic substances (artificial chromogenic or fluorogenic substrates) to solid nutrient media changes the color of the micro-colonies or makes them fluorescent. Some microorganisms like *E. coli* O:157, *Staphilococcus aureus*, and *Salmonela* grows on "Chromagars," (Hardy Diagnostics, Inc. CA, CROMagar Company, France) a solid or semi-solid nutrient media that specifically changes the color of investigated microorganisms because of artificial substrates for unique enzymes added to media. These substrates are non-toxic to the cells and allow normal growth. Toxic artificial substrates such as Tetrazolium salts, Fluorescein diacetate and other substances can not be used because stops cells growth. Chromagars' time of incubation is typically 24-120 hours, which is not considered rapid.

Detection and enumeration of colonies are done visually with a naked eye or with magnifying devices. Visual detection and enumeration using magnifying devices requires relatively big colonies; from hundreds of microns to millimeters in diameter. Microscopy helps to find micro-colonies that are smaller in size, however, these colonies must be at least tens of microns in size, contain at least several hundred cells, and require at least 10-12 hours of incubation. Additional coloration of these micro-colonies is difficult because cells spread/wash away on the surface when dye solution applied. It is also difficult to find them on a big surface of plate.

Detection of microorganisms could also be achieved by dividing a sample into many discrete zones, adding liquid nutrient media, incubating from many hours to days, adding indicator substance or counting turbid zones, and calculating concentration (U.S. Pat. No. 5,716,798). This method gives a reduction of growth of only 20-40% because employed relatively large volumes of discrete zones, consisting of large wells on the side of a special flask for growth. A 90% of zone volume related to nutrient media and therefore analyzing sample could be only several milliliters. Therefore, this method is used only for the detection of microbes in human blood because blood samples are very small and their contamination is in a range from single cells to several hundred cells per milliliter. The same idea used in SIMPLATE™ device (Biocontrol Systems, WA, USA)—device for growth of microorganisms in liquid media divided on several tens smaller volumes (U.S. Pat. Nos. 5,518,892, 5,620,895 and 5,753,456). The time of incubation in the SIMPLATE™ device is 24 hours.

The modern microbiology employs some methods to shorten time for microorganism growth and to improve the visibility of colonies, for example, employing optimal growth nutrient media, adding chemical matter in the nutrient media, or employing optical instruments or devices. However, there are no methods utilizing the shape of the colony during its growth in order to enhance its optical density (light absorbance) or fluoresence. The shape of a regular micro-colony is usually semi-sphere. See FIG. 1A. Changing a colony's shape from a regular semi-sphere with a large volume and a large amount of cells to a thin cylinder shape with a small volume and a small amount of cells will strongly reduce the time between inoculation and colony counting. Smaller amounts of cells need a shorter time for their production. The usage of chemicals producing color or fluorescence and optical instruments together with detection of cylindrical colonies would improve visibility and reduce the time required for analysis.

Therefore, there remains a need in the art for new methods and apparatus of early microorganism detection that have quicker microorganism recognition time than existing methods and apparatuses.

SUMMARY OF THE INVENTION

The present invention is directed to a new method and device for rapid detection of cellular microorganisms during their preliminary short growth on or in nutrient media.

It is an object of the present invention to change the natural shape of micro-colonies to a long cylindrical shape by growing the colonies in long and extremely small micro-channels that enhances the optical characteristics of the micro-colony and strongly improves the micro-colony's visibility (detectability) with microscope.

It is a further object of the invention to provide an array of micro-channels on a glass plate to trap microorganisms for growth therein, and to provide early visibility. Enhancing of the visibility (detectability) of the micro-colonies shortens the time between inoculation and detection of the colony in several times but retain reliability of analysis.

It is a further object of the invention to provide thin, long micro-channels that are open on both ends. A large volume of sample is filtrated through a micro-channel plate. The extremely small volume of the micro-channels reduces the required growth time to 1-5 hours prior to detection. Growth of microorganisms within these long, thin micro-channels changes the optical characteristics of micro-colonies much faster than growth of micro-colonies in a large flat volume or well that in millions times larger.

This invention differs from prior methods of detection of colonies by using a glass plate containing hundreds of thousands of extremely small and long micro-channels that are open from both ends. The combination of a micro-channels and a filter allows cells to be trapped on the surface of the filter, thus allowing colonies to grow inside the micro-channels. Colonies grown inside the micro-channels will obtain a tall cylindrical shape, increasing light absorbency with a smaller volume and cell number than if grown on a flat surface, drastically reducing the amount of time required for analysis. This method is realized with a simple device consisting of a multiplicity of micro-channels, a filter to trap cells by filtration from air or liquid, and a frame consisting of several parts.

These and other objects of the invention will be more fully understood from the following description of the invention on reference to the illustrations appended hereto.

BRIEF DESCRIPTION OF THE DRAWINGS

FIG. 6B is a photograph of micro-colonies in micro-channels wherein the micro-colonies are colored by chromogenic substrates.

FIG. 6C is a photograph of micro-colonies in micro-channels wherein the micro-colonies are colored fluorogenic substrate or fluorescent dye.

FIGS. 6D, 6E, and 6F are illustrations of the direction of light travel through the filter and microchannels.

FIG. 7 photograph of bubbles of Oxygen produced by micro-colonies in reaction Catalase—Hydrogen Peroxide.

DETAILED DESCRIPTION OF THE INVENTION

As used herein, "long" micro-channel here means cylindrical hollow micro-channel with ratio of inner diameter to length=1/10–1/100.

As used herein, "extremely small" means volume range 1-500 picoliters ($1/10^9$–$1/5 \cdot 10^7$ of one milliliter).

The term "colony" or "micro colony" in microbiology means a group of cells appearing from one single cell and consisting only from descendants of that cell.

As used herein, the term "cell layers" refers to cells within a channel that occupy about the same height level, wherein another layer of cells can be supported above the layer. Each cell layer in a micro-channel of diameter 10 μm consists of 20-80 cells.

Figure 1:
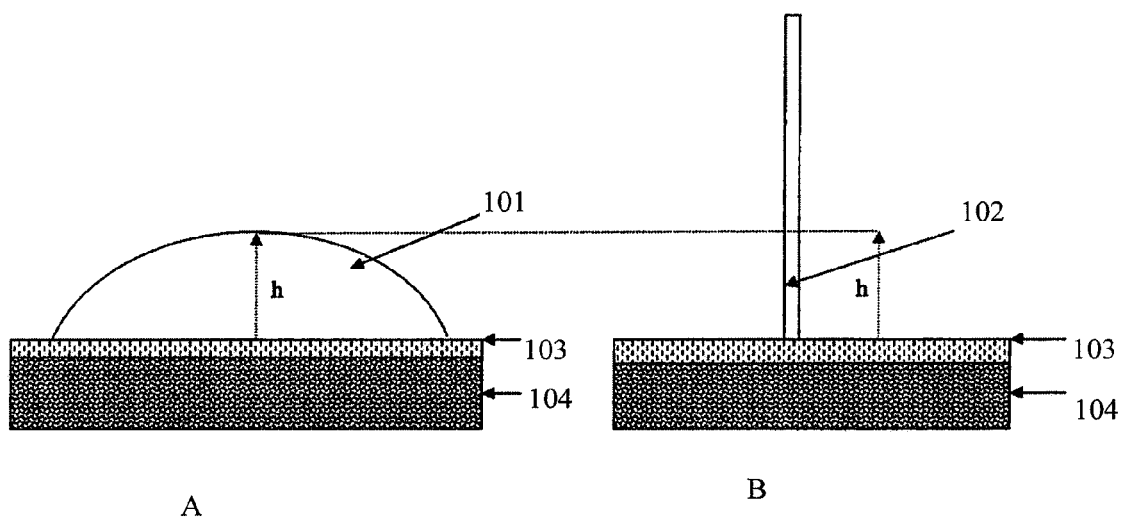
FIG. 1A is a side-view of prior-art colony having a semi-sphere shape.
FIG. 1B is a side-view of a long, extremely small micro-channel above a filter and nutrients.

The shape of a regular prior art micro-colony is usually semi-sphere 101 (FIG. 1A), in contrast to one embodiment of the present invention as a long, extremely small micro-channel 102 located on filter 103, which in turn is located on media, or Agar, 104 (FIG. 1B). Thus, a micro-colony inside microchannel 102 in the embodiment of the present invention is notably thinner than the micro-colony of the prior art semi-sphere 101 shown in FIG. 1A. A colony inside micro-channel 102 (FIG. 1B) reaches height h much quicker than a colony would reach the same height h in semi-sphere 101 (FIG. 1A). The height (or thickness) of micro-colonies is crucial to visibility using microscopy as a high (thick) colony has a greater light absorbance, which is the most important optical characteristic of visibility. A long and thin micro-colony has the same light absorbance as a regular semi-spherical colony of the same height-h. At the same time, a volume and number of cells at height h in micro-channel 102 (FIG. 1B) is much less than in semi-sphere 101 (FIG. 1A) at height h, and therefore the time of incubation to create a visible colony is in micro-channel 102 (FIG. 1B).

Calculations show the advantage in reducing the time of growth in micro-channel 102 (FIG. 1B) compared with semi-sphere 101 (FIG. 1A). A regular shape of colonies growing on flat surfaces of solid nutrient media is, usually, near to semi-sphere. The volume of a semi-sphere (Vss) is $Vss = \pi \cdot h^2 \cdot (R - h/3)$, where Vss—volume of semi-sphere, R—radius of sphere, ¶—π or pi, and h—part of radius—height of semi-sphere. The volume of a cylindrical colony (Vcc) such as in micro-channel 102 (FIG. 1B) is $Vcc = \pi \cdot R^2 \cdot h$, where R-radius of cylinder, h-height of cylinder.

Micro-colony with height (h) 10 μm and R=20 μm has volume:

$$Vss = 3.14 \cdot 10^2 \cdot (20 - 10/3) = 5234 \text{ μm}^3$$

Cylindrical colony with the same height (h=10 μm) and R=2.5 μm has volume:

$$Vcc = 3.14 \cdot 2.5^2 \cdot 10 = 196 \text{ μm}^3$$

Thus, the volume of a cylindrical colony is smaller than the volume of semi-spherical micro-colony with the same height by 27 times, yet both have the same light absorbance. The volume of one cell of *Escherichia coli* (*E. coli*) is near to 1 μm³. The speed of multiplying of *E. coli* is around 20 min at optimal temperature, on optimal media. One cell of *E. coli* can produce 8 cells in one hour, 64 in two hours, 512 in 3 hours, 4096 in 4 hours and 32768 in 5 hours. Thus, one visible micro-colony on a flat surface, containing 5234 cells, can be formed in 4.2 hours. The cylindrical colony with the same height and light absorbance (96 cells) can be formed in 2.5 hours. Therefore, the growth of micro-colonies with a cylindrical shape has a significant advantage as visualization of colonies can be done at much earlier stages.

The visualization of microorganisms in one or a multiplicity of micro-channels is much faster than in Petri plate, regular laboratory tubes, wells or semi-spheres of an immunological plate, or other known laboratory devices for microorganism growth, because of the very small volume of micro-channels and their long cylindrical shape. Thus, one cell trapped in a cylindrical micro-channel, with a length 500 μm and diameter 10 μm (V=40,000 μm³, corresponds to a concentration of 25 million cells per ml (V=10¹² μm³). Forty cells in a micro-channel correspond to the concentration 10^9 cells per ml, which is a well-detectable concentration. One cell of *E. coli* can reach this concentration from one trapped in micro-channel cell (40 cells per micro-channel=10^9 cells per ml) in 1.7 hours.

Experiments show that 10 cell layers of colorless small cells (for example *E. coli*) are enough to find visual differences between micro-channels containing cells and empty micro-channels using a regular light microscope, even with a small magnification X100. A smaller diameter of micro-channel requires a smaller amount of cells to create 10 cell layers in the micro-channel. Table 1 represents the number of layers of *E. coli* that can be produced in micro-channels of different diameters between one and five hours.

TABLE 1

Correlation between time of forming cell layers in micro-channels and diameter of micro-channel (*E. coli*, growth at 37° C. on TSA; the time of multiplication ~ 20 min)

| Diameter of micro-channel | Hours of Incubation | | | | |
|---|---|---|---|---|---|
| | 1 hour | 2 hours | 3 hours | 4 hours | 5 hours |
| 2 μm | 3 cell layers | 21 | 171 | 1365 | 10920 |
| 3 μm | 1 | 9 | 73 | 585 | 4680 |
| 4 μm | 0.6 | 5 | 39 | 315 | 2520 |
| 5 μm | 0.4 | 3 | 26 | 205 | 1640 |
| 7 μm | 0.2 | 2 | 13 | 108 | 860 |
| 10 μm | 0.1 | 1 | 6 | 50 | 410 |

Extrapolated, table 1 shows that 10 cell layers will be reached in a micro-channel with a diameter of 2 μm 1.5 hours; in a 3 μm microchannel in 2 hours; in a 4 μm micro-channel, in 2.3 hours; in a 5 μm micro-channel in 2.7 hours; in a 7 μm micro-channel in 2.9 hours and in a 10 μm micro-channel in 3.5 hours. Thus, the detection and enumeration of long cylindrical micro-colonies, according this invention, can be done 10-20 times faster than regular growth, detection and enumeration of colonies.

Figure 2:
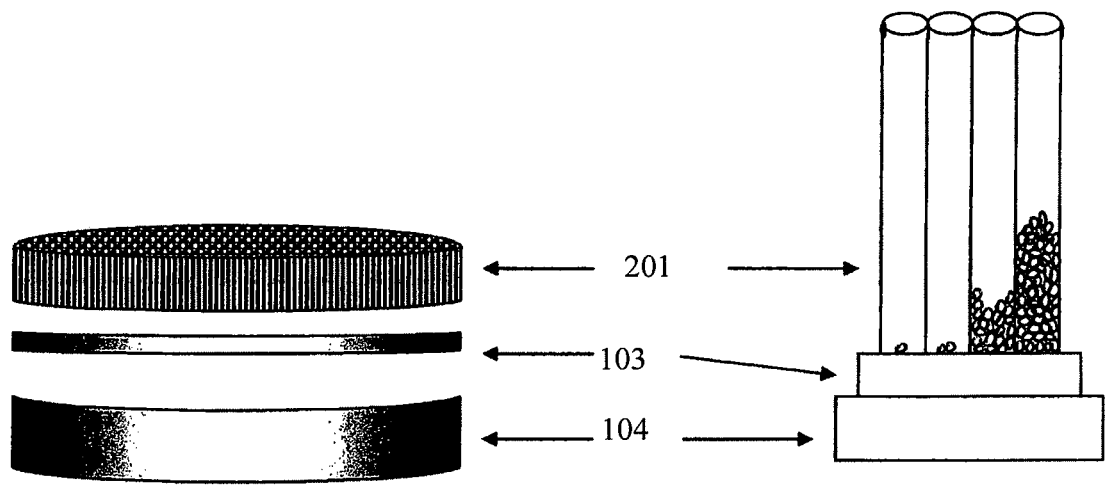
FIG. 2 is an exaggerated side-view of a multiplicity of micro-channels forming an array of micro-channels.

The growth of a cylindrical micro-colony can be made in a microarray of micro-channels as shown in FIG. 2. The diameter of each of these micro-channels needs to be very small, only 10^4-10^5 times larger than the size of the cells. Array 201 (FIG. 2) is also called a Micro-Channel Glass Plate (MCGP). MCGP 201 contains a multiplicity of micro-channels in any required shape. While a round MCGP 201 is depicted in the figures, any shape MCGP 201 can be used, for example, a square or rectangle one. In one embodiment, MCGP 201 has 700,000 micro-channels per cm². Preferably, each micro-channel in MCGP 201 has a diameter of about 10 microns, and a length of about 500 microns. In general, MCGP 201 is above filter 103, wherein filter 103 is porous, such that the pores are smaller than the cells in an aqueous sample (FIG. 2). As the sample is filtrated from above MCGP 201 through both MCGP 201 and filter 103 in a filtration process, a liquid portion of the aqueous sample filters through filter 103 while cells are trapped in micro-channels of MCGP 201 on the surface of the filter 103. After the filtration is completed, the MCGP 201 and filter 103 is placed on a nutrient agar or agar block of solid nutrient media 104. Nutrient substances from the media penetrate the filter, and fill all micro-channels. Growths of micro colonies generally start after this penetration.

Figure 3:
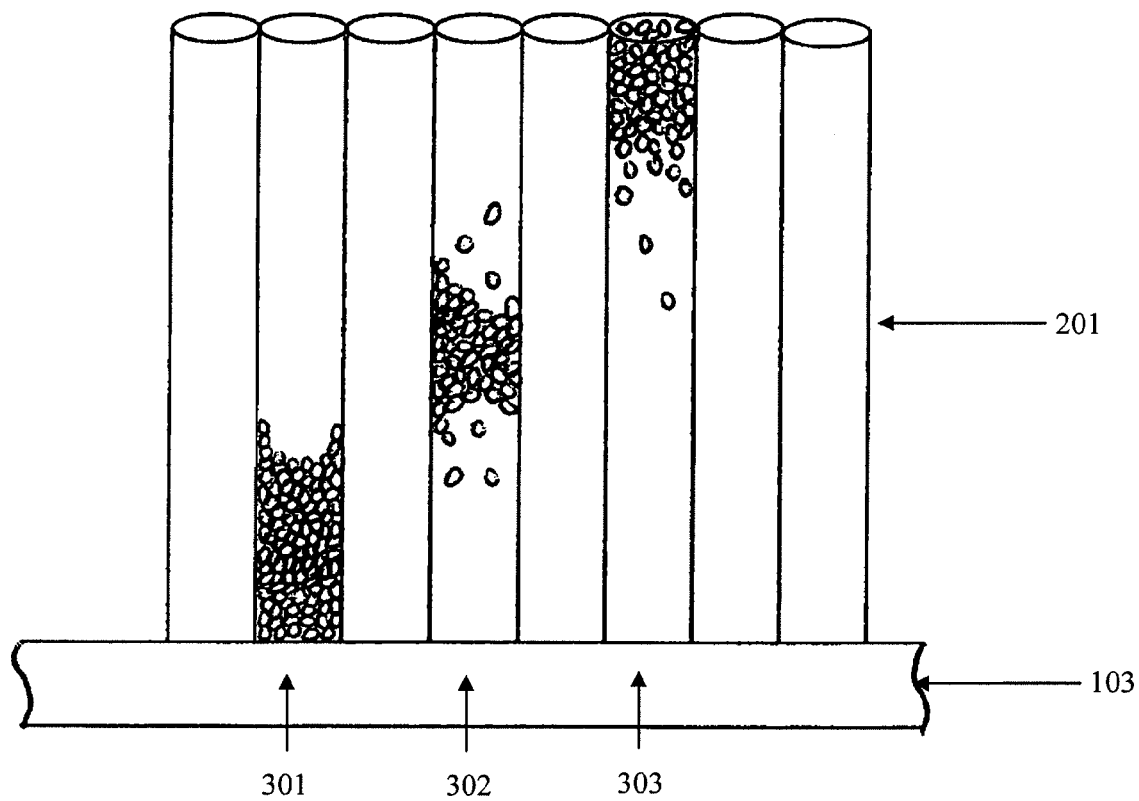
FIG. 3 is an exaggerated side view of a multiplicity of micro-channels showing three different positions of an initially trapped cell in a micro-channel and micro-colonies.

A micro-colony can start formation regardless of initial trapping position within a micro-channel. FIG. 3 shows three typical positions of a cell in a channel. 301—cell was trapped on the surface of the filter 103 and colony formed from the bottom of micro-channel of MCGP 201. This formation appears when nutrient substances just moistens filter. 302—cell was trapped on the wall of micro-channel of MCGP 201 by the force of adhesion or by antibody attached to the wall preliminary to filtration.

The formation of a micro-colony starts only if the micro-channel is completely filled by nutrient substances from wet agar media, or a thick paper filter filled by a nutrient broth. 303—cell was trapped on the filter 103, but was later raised up by liquid media and started forming micro-colony in micro-channel of MCGP 201. In all of these cases, one cell formed a micro-colony of cells that were descendants of the first cell in the solid, semi-solid or liquid culture.

Figure 4:
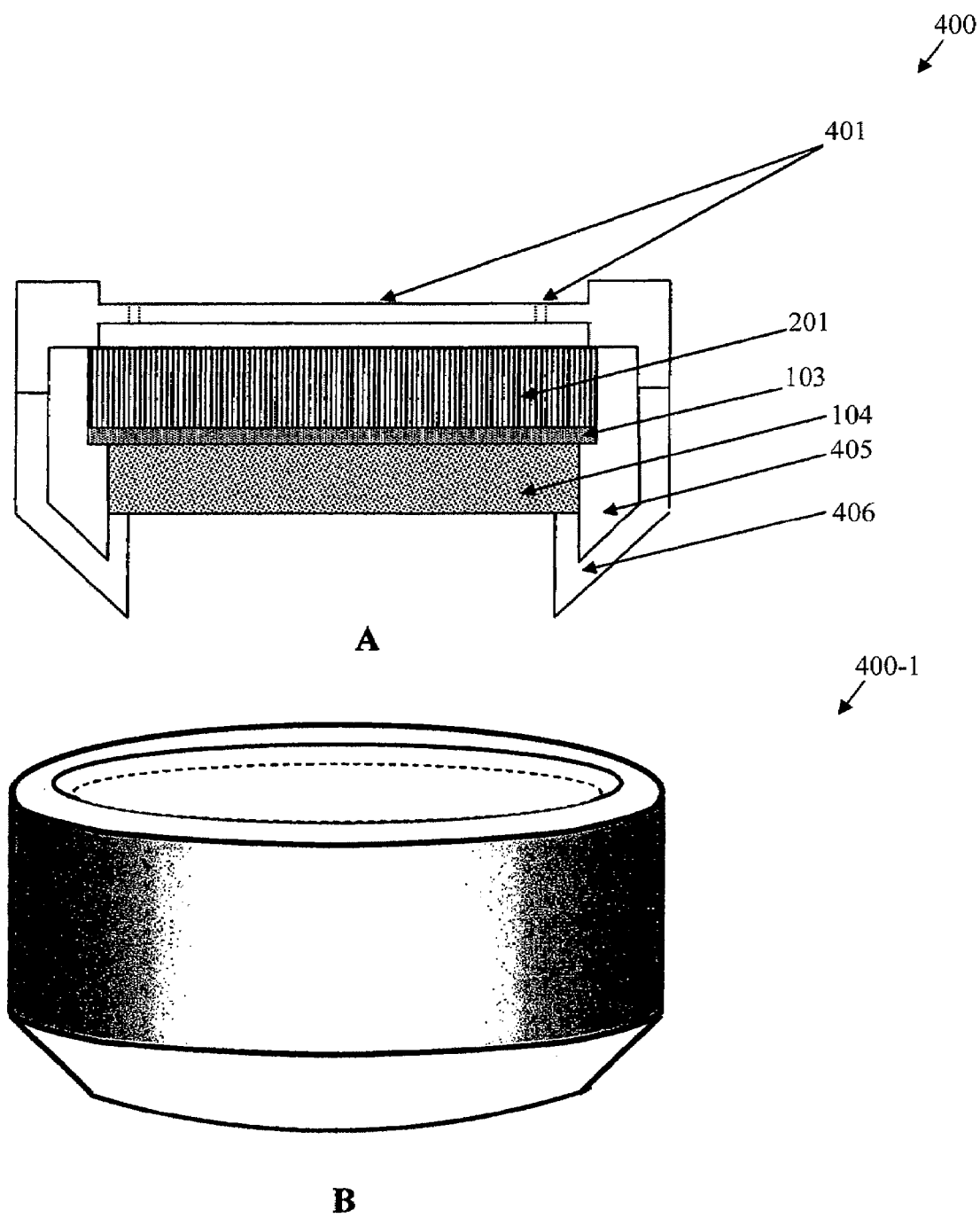
FIG. 4 is view of a sampling-detection unit (SDU). View A is a cross-sectional view of the SDU. View B is an isometric view of the SDU.

FIG. 4 shows a preferred embodiment of a sampling-detection unit (SDU) (View A is a cross-sectional view of SDU 400; View B is an isometric view of SDU 400-1) used to trap cells by filtration from liquid or air, grow micro-colonies, and/or treat colonies with chromo- or fluorogenic substrates if needed. SDU 400 preferably includes a removable transparent plate 401, wherein the plate can be glass, plastic or other transparent substance. Transparent plate 401 includes one or more small holes for respiration. SDU 400 further includes MCGP 201 filter 103, porous support 104, a holding device 405, wherein holding device 405 holds MCGP 201 and filter 103, and holding device feature 406, wherein holding device feature 406, holds porous support 104 adjacent to filter 103. Holding device feature 406 and transparent plate 401 are readily removable from holding device 405, filter 103 and MCGP 201. Further, porous support 104 can be supported by holding device feature 406 with or without the further inclusion of holding device 405. As could be readily understood by one skilled in the art, the precise shape and structure of SDU 400 and 400-1 can vary while still maintaining the spirit of the invention, particularly with regard to porous support 104 and holding devices 405 and 406.

Figure 5:
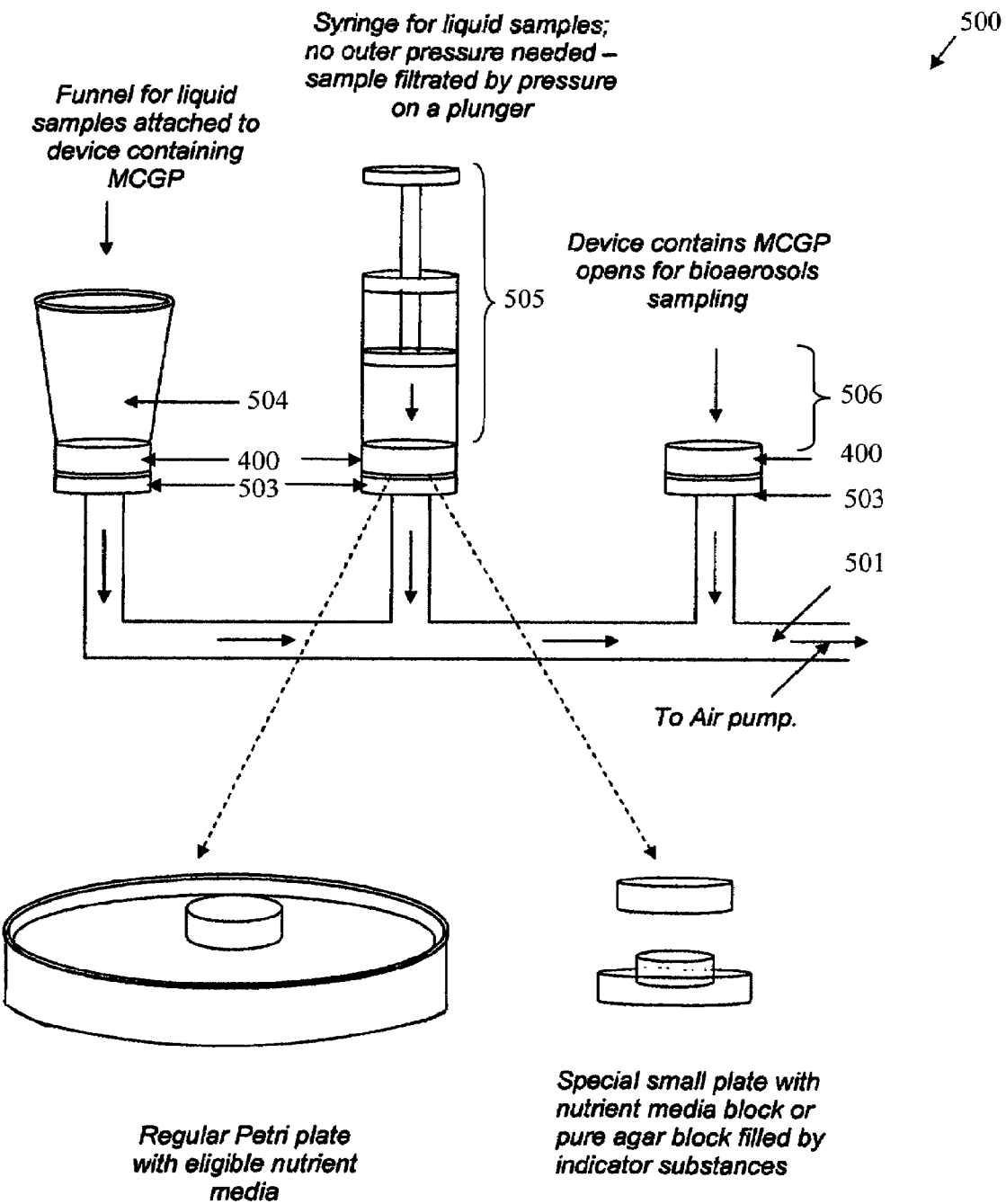
FIG. 5 is a side view of a filtration process and method used for filtrating of liquid samples, air samples, or syringe for filtration without using outer air pressure.

FIG. 5 shows filtration device 500 consisting from manifold 501, SDUs 400 and holder/funnel support 503 for SDUs. One or a multiplicity of SDUs 400 are adjusted to manifold 501 as shown in FIG. 5, wherein SDUs 400 are placed on funnel support 503 of manifold 501 after removal of transparent plate 401 (FIG. 4). FIG. 5 shows different adjustments to the SDU 400 mounted on manifold 501 for filtration, wherein SDU 400 can be operated with funnel 504 for filtration of liquid samples which can be adjusted to the SDU 400 syringe 505 for passing liquids with a help of plunger, or just for passing small samples, or without any additional devices as it is intended for air filtration 506 for example, for trapping bioaerosols (cells and spores) in micro-channels.

Filtration device 500 is shown to include three separate funnel supports 503, wherein one is used to support SDU 400 with a funnel 504, one for an SDU with a syringe 505, and one for neither 506. As could be reality understood, filtration device can consist of one or any number of funnels supports 503 in any arrangement, wherein the SDUs 400 placed on funnel supports 503 can further include any combinations of funnels 504, syringes 505 or neither 506.

To use the filtration device, a liquid or air sample containing microorganisms is filtrated through the device adjusted to manifold. After adding sample, transparent plate 401 (FIG. 4) must be placed back on SDU 400 to resist contamination.

After filtration, each SDU 400 is removed from funnel support 503 (FIG. 5). SDU 400 is disassembled into porous support and holder, then transparent plate 401 (all shown in FIG. 4) is returned back on a top of SDU 400. SDU 400 is placed on the surface of an eligible solid nutrient media or in the container with a liquid nutrient media, for example, placed on a Petri plate with nutrient media (bottom left, FIG. 5) or nutrient media agar cylinder adjusted to lower side of filter (bottom right, FIG. 5) to initiate micro-colony formation. One embodiment of this is shown in FIG. 2 where liquid from nutrient agar 104 immediately wets filter 103. and penetrate micro-channels of MCGP 201 because of strong capillary forces. The nutrient media is absorbed by the filter and supports the growth of a cylindrical-shaped micro-colony or penetrates through the filter in channels, and supports the growth of suspended microorganisms that later forms cylindrical solid or semi-solid micro-colony as shown on the FIG. 3.

The SDU with nutrient media is incubated at an appropriate temperature for the required time for cell growth, wherein the temperature and time needed will vary as is known in the art with regard to what type of colonies are being grown. In order to reduce the time of analysis by increasing light absorbance or adding fluorescence, the device can be placed in a container with an eligible solution of artificial substrate. Otherwise the substrate can be added to solid nutrient media in advance as it is done in Chromagars.

This invention is capable of detecting a range of cells in a sample from a single cell to several hundreds of thousands or even millions, depending on the number of micro-channels in the MCGP. For example, a 25 millimeter diameter MCGP with micro-channels 10 µm in diameter (square of plate around 5 $cm^2$ and 700,000 micro-channels per one $cm^2$) contains 3.5 millions of micro-channels. In order to have reliability, the number of cells in a sample should be less than the number of micro-channels in MCGP, thereby keeping the allowing no more than one cell per micro-channel. In further preferred embodiments, a ratio of about one cell per five to ten micro-channels is used, to greater ensure that only one cell will enter any particular micro-channel. Thus, for example, with a MCGP having 3.5 million micro-channels, the number of live microbes in a sample would not exceed 700,000 for this plate so that one cell goes to one micro-channel with higher level of reliability. If a sample is expected to contain a higher concentration of microbes, it can be diluted in a manner regularly used in microbiological practice. In comparison, a regular Petri plate limits colony growth from one single colony to only 300 colonies recommended by US Food and Drugs Administration, otherwise colonies will begin to overlap each other and decrease the reliability of enumeration. Thus, current invention allows grow and detect in around thousand times more concentrated samples without ten-fold dilutions: about 700,000 with MCGP and only around 300 by regular Petri plate.

Figure 6:
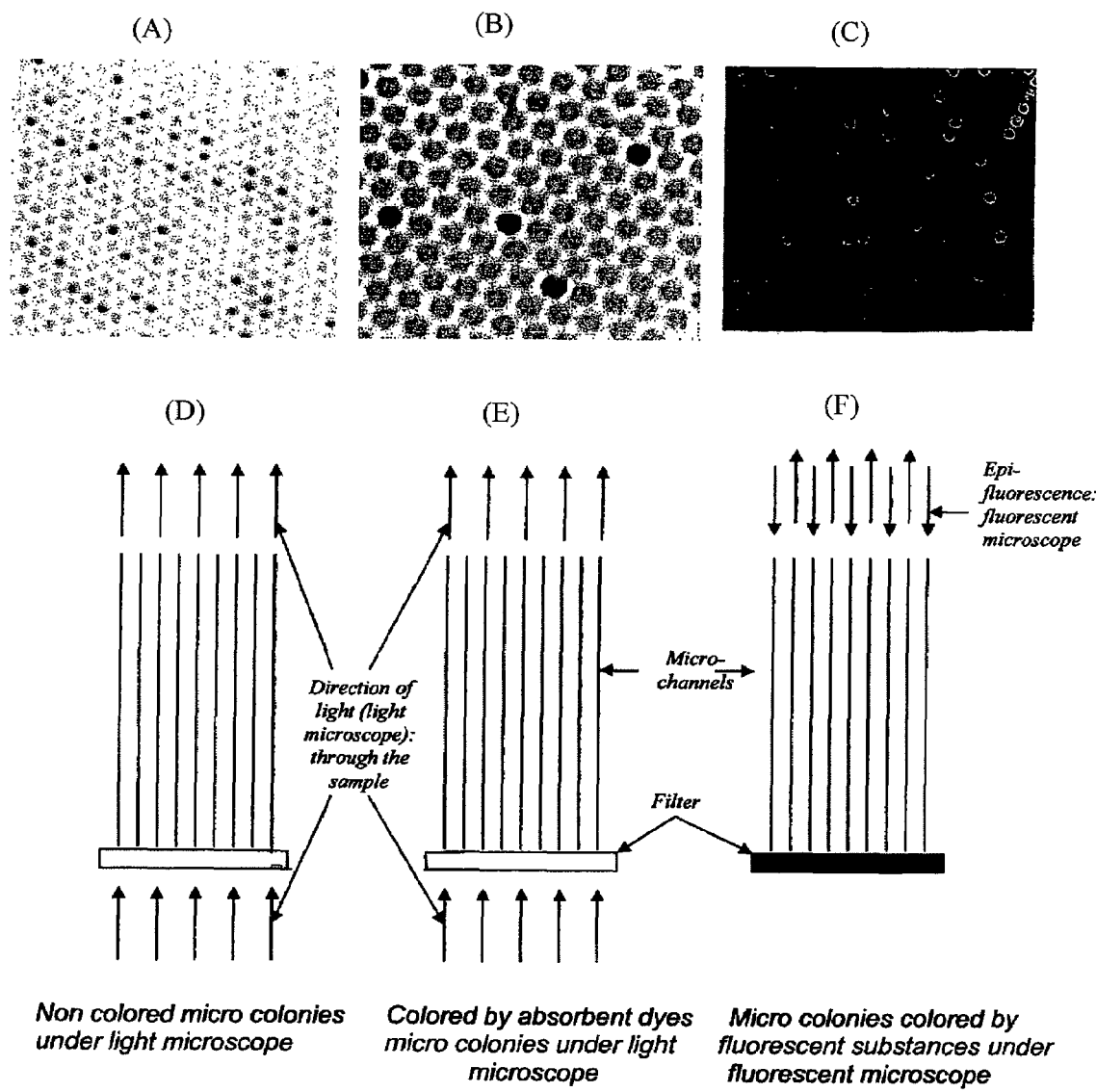
FIG. 6 shows micro-channels with micro-colonies. (A) is a photograph of micro-colonies in micro-channels showing no coloration. (B) is a photograph of micro-colonies in which the micro-colonies are colored by chromogenic substrates. (C) is a photograph of micro-colonies in micro-channels in which the micro-colonies are colored with a fluorogenic substrate or fluorescent dye. (D) illustrates non-colored micro-colonies under a light microscope. (E) illustrates micro-colonies colored by absorbent dyes under a light microscope. (F) illustrates micro-colonies colored by fluorescent substances under a fluorescent microscope.

The micro-channels containing colonies appear as dark dots when a regular light microscope is used, as shown in FIG. 6A. The addition of artificial chromogenic or fluorogenic substrates to micro-colonies can reduce the time between inoculation and detection as they make micro-colonies much more visible at an earlier stage. FIG. 6 shows the differences between natural non-colored micro-colonies (FIG. 6A), micro-colonies colored by chromogenic substrates or absorbent dyes (FIG. 6B), and micro-colonies colored by a fluorogenic substrate or a fluorescent dye (FIG. 6C). The coloration of micro-colonies inside micro-channels is done by attaching agar or filter paper treated with required substances to the opposite side of the filter attached to the micro-channel plate. A light microscope sends light through the MCGP (colorless), filter(colorless), and agar (light microscope) (FIGS. 6D and 6E), revealing long cylindrical shaped micro-colonies because of the natural light absorption of cells, or due to cells colored by chromogenic substrates or absorbent dyes. A fluorescent microscope (FIG. 6F) sends a shorter wave light (ultra violet, blue or other depending on dye) and accepts long waves of fluorescence (blue, green or red). Therefore, micro-channels with micro-colonies will appear as bright dots on a dark background. The structure of the SDU for fluorescent version is: MCGP (black non fluorescent), filter (black non-fluorescent), and agar (filled by fluorescent indicator). Fluorescence is considered a much more sensitive type of analysis. Thus, the micro-colonies can be much smaller/shorter than those analyzed with the use of light absorbance.

FIGS. 6D, 6E, and 6F are illustrations of the direction of light travel through the filter and microchannels. Whether fluorescent or color indicators are used or not used, and SDU is placed under a light or fluorescent microscope, and the amount of dark, colored or fluorescent channels is detected and enumerated. This amount corresponds to the number of cells trapped on the surface of the filter. The difference between non-colored micro-colonies (FIG. 6A,) micro-colonies colored by chromogenic substrates or colored by light absorbent dyes (FIG. 6B,) and micro-colonies colored by fluorogenic substrates or fluorescent dyes (FIG. 6C.)

Many different dyes and indicators used for coloration of micro-colonies. Including but not limited to:

Colorless Fluoresceine diacetate or Fluoresceine butirate cleaves by Esterases with the release of highly fluorescent Fluoresceine (green fluorescence=515 nm). Fluoresceine collects (crystallizes) inside cells and interrupts biochemical pathways, which cause a death of cell. Thus, Fluoresceine diacetate and other Fluoresceine derivatives can be used only after micro-colonies are formed.

Colorless 4-Methylumbelliferyl acetate, -butyrate, -propionate, or -phosphate cleaves by Esterases, Lipases or Phosphatases with the release of 4-Methylumbelliferone, a highly fluorescent substance (blue fluorescence=450 nm). 4-Methylumbelliferone is secreted from cells and concentrates in extracellular spaces, filling the remaining volume of the micro-channel. FIG. 6C demonstrate micro-channels-filled by 4-Methylumbelliferone appeared after enzymatic reaction of E. coli micro-colony with 4-Methylumbelliferyl-butirate. Thus, 4-Methylumbelliferyl derivatives can be used during micro-colony growth. Extracellular buildup of fluorescent signal; can significantly reduce the time required for analysis very small micro-colonies (10-20 cells) can be detected. To grow micro-colony with 10-20 cells needs only 2-2.5 hours of incubation.

A big group of Tetrazolium salts—indicators of dehydrogenases (group of respiratory enzymes of live cells was successfully used to color micro-colonies: Thiazolyl blue, Tetrazolium iodo (INT), Nitrotetrazolium blue (NBT), and BT-tetrazolium. Non colored Tetrazolium salts produce well colored Formazans (dark violet, blue, red, pink) in reactions with live cell's dehydrogenases. Our experiments show that Thiazolyl blue tertazolium salt is the best and universal for all investigated microorganisms.

Chromogenic substrates such as 5-Bromo-4-chloro-3-indoxyl butyrate, -palmitate, -phosphate (blue precipitates inside cell) or 6-Chloro-3-indoxyl butyrate, -palmitate (red color precipitates) for Esterases, Lipases, or Phosphatases, as well as other chromogenic substrates can be used for coloration of formed micro-colonies and as additives to nutrient media Chromogenic substrates that are dissolved in nutrient media before application for cell growth are referred to as "Chromagars." However, Chromagars are created for only a few microorganisms: CHROMagar™ Candida, CROMagar™ O157, CHROMagar™ Salmonella, CHROMagar™ Staph aureus and CHROMagar™ Orientation for urinary tract pathogenic microorganisms (CROMagar company, France).

Dyes, such as Dansylchloride (DNS-chloride) or Fluorescamine, are capable of increasing fluorescence hundreds or even thousands times after attaching to biomolecules such as NH— groups of proteins. These compounds are also useful for marking micro-colonies for further enumeration.

Some substances are known to change the color of colonies to a dark or even black color, making micro-colonies more visible on a Petri plate or under a microscope in micro-channels. For example, iron sulfide in SPS Agar is known to color Clostridia, and XLT4 Agar Base colors Salmonella. Likewise, potassium telluride in VJ Agar colors Staphylococcus aureus colonies in well visible black color.

Some light absorbent and fluorescent substances reveal ability to change color or fluorescence after pH of medium changes. Micro-colonies change inner pH in micro-channel that can be found with color or fluorescent indicators.

Growth of 5-6 hours is often enough to produce long micro-colonies, and detect and enumerate a large number of non-colored micro-colonies by their enhanced light absorbance or light scattering. For example growth of E. coli in micro channels on TSA around 6 hours at 37° C. is enough to produce micro-colonies visible without of additional coloration.

Physical factors can also be changed to decrease the time between inoculation and micro-colony detection. For example, heating to coagulate proteins, increasing light absorbance or light scattering, or adding substances to produce gas bubbles within micro-channels that contain live cells—such as Oxygen ($O_2$) from Hydrogen Peroxide ($H_2O_2$) by Catalase—can be employed. FIG. 7 demonstrates bubbles of Oxygen produced by micro-colonies in reaction Catalase—Hydrogen Peroxide of Bacillus megatherium, incubated 3 hours on TSA at 35° C.

Many different kinds of samples, a variety of microorganisms, hundreds of nutrient media, and a multitude of indicator substances opens a huge opportunity for the implementation of this invented technology in the different areas of microbiology.

EXAMPLE 1

Detecting and Enumerating Live Bacteria in Liquid Samples

One of the mostly used nutrient solid media for detection of total viable organisms (mainly bacteria) is Tryptic Soy Agar (TSA). Regular growth of colonies on a Petri plate filled with TSA requires 24 to 72 hours at 35° C. Using the proposed invented method; incubation requires only 4 hours. The procedure for the invented technology is as follows:

The sample (100 milliliters) is filtrated through the SDU, trapping cells in micro-channels containing a colorless MCGP and colorless filter (Polycarbonate, 0.2 microns pores, Osmonics Inc, USA) (FIG. 4, FIG. 5). Live cells, if any in the sample, are trapped in some of the micro-channels.

The SDU is removed from the manifold and a nutrient media (TSA) agar block is attached to the surface of the filter. Nutrient substances from the TSA saturate the filter and penetrate into micro-channels. This process takes around 10-30 seconds.

The SDU with attached agar block is placed in an incubator for 4 hours at 35° C. Trapped live cells form long and thin micro-colonies in micro-channels where they were trapped.

After incubation, the nutrient media agar block is removed. Another agar block containing Thiazolyl blue tetrazolium salt (3 mg/ml) is adjusted to the filter. Alternatively, a thick filter paper filled by an indicator substance can be used instead of agar block. Yellowish molecules of Thiazolyl blue penetrates (diffused) into the micro-channels. Any micro-channels containing micro-colonies become dark violet in color (FIG. 6B). The reaction of tetrazolium salt with cells is well-known and based on respiratory enzymes—dehydrogenases of living cells accepting a Hydrogen atom (H+) from the tetrazolium ring for further use in respiration. This reaction then results in a colored substance—Formazan, which is collected inside live bacterial cells, mainly in mesosomes. All known bacterial and fungal cells react with tetrazolium salt to reveal this color reaction. Intensely colored long cylindrical micro-colonies are much more visible than the same non-colored micro-colonies or colored flat micro-colonies (grown without micro-channels). An agar block (2% in distilled water, 1 cm$^3$ volume) can be prepared with Thiazolyl blue by adding 3-4 drops of a 3 milligrams per milliliter Thiazolyl blue in phosphate buffer (pH=7.2). Intensively colored cylindrical Micro-colonies are visible as colored circles and are easily enumerated in a regular light microscope with a microscopic multiplication from X40 or larger. The concentration (cells per milliliter) of live cells in a sample is enumerated or calculated by regular known methods: direct count, "most probable numbers", or by counting of several microscopic fields, calculate average and recalculate on all surface of MCGP. Also automatic count is possible with several modern microscopes equipped by image analyzing programs.

Thus detection and enumeration of microorganisms in a sample by micro-colonies method and device can be completed many times faster than when depending upon cell growth on a regular Petri plate.

EXAMPLE 2

Identification of Micro-colony of *E. coli* O:157 by Enzyme Immunoassay in Micro-channels Micro-colonies can be identified in the micro-channels using enzyme immunological analysis (EIA). Cells are trapped in the micro-channels by filtering a sample as described in Example 1. The use of EIA for the identification of micro-colonies is based on the immunological reaction between antigens of the cells (micro-colony) and enzyme-antibody conjugates. The conjugate is passed through the micro-channels in order to perform antibody—antigen reactions. The syringe shown in FIG. 5 is suitable for this because it allows a small volume of conjugate to be slowly pressed through the micro-channels. The micro-colonies in this case must be very small, 8-32 cells, as larger micro-colonies can clog the micro-channel. After the conjugate attaches to *E. coli* O:157 antigens, a block of pure agar filled by Tetramethylbenzidine (a substrate for Horseradish Peroxidase—an enzyme of the conjugate) is attached to the filter. Tertamethylbenzidine is cleaved by the Horseradish Peroxidase with creation of a blue-colored dye that collected in micro-channel with *E. coli* O:1.57. The number of *E. coli* O:157 present in the sample corresponds to the number of blue micro-channels. This example is based on a well known color reaction, but fluorescent reactions are also available. Thus a conjugate consisting from antibody and β-D-Galactosidase gives a fluorescent 4-Methylumbelliferone in reaction with 4-Methylumbelliferyl-β-D-Galactose. Conjugates consisting from an antibody and Phosphatase produce 4-Methylumbelliferone in reaction with 4-Methylumbellyferyl phosphate, disodium salt.

EXAMPLE 3

Sampling, Detection and Enumeration of Bioaerosols

Micro-channel technology can also be used for the rapid analysis of bioaerosols. Air is filtrated through the SDU, which is adjusted to the manifold. The manifold is connected to an air pump (AirCheck HV30, QuickTake 30 or another, SKC Inc., USA). A rotameter for measuring the air volume is installed between the manifold and the pump. A required volume of air is passed through the SDU, and microorganisms present in the air sample are trapped in the micro-channels. Bacilli and Fungi spores are considered the main microorganisms in bioaerosols. Thus, two nutrient media need to be used, TSA for Bacilli and SDA for Fungi spores. This also requires using two SDU. Dormant spores of Bacilli usually germinate within 0.5-1.5 hours after contact with a nutrient media. This time needs to be added to the regular time of Bacilli incubation trapped in micro-channels (4 hours) in order to form a cylindrical micro-colony from the spore. Germination of Fungi spore requires about 2-6 hours, followed by incubation in the SDU of about 12 hours. After micro-colonies from spores appear in the micro-channels, procedures described in Example 1 (detection of the total number of viable microorganisms) or Example 2 (identification of micro-colonies) or other procedures developed for micro-channel analysis take place. Another version of sampling air microorganisms is by first sampling in liquid (sodium chloride solution, buffer, liquid nutrient media) with help of well-known liquid samplers (e.g., AGI-30, SKC BioSampler, SKC Inc., USA) and then filtrated through the SDU. Currently used methods for bioaerosol detection are based on "landing" particles on the surface of agar media (Impactor BioStage, SKC Inc.) or inoculating liquid samples with microorganisms sampled beforehand. Both methods need a long growth period for the microorganisms in order to form well visible colonies: 24-72 hours for bacteria and 72-120 hours for fungi.

Whereas particular embodiments of the invention have been described herein for purposes of illustration, it will be evident to those skilled in the art that numerous variations of the details may be made without departing from the invention as defined in the appended claims.

What is claimed is:

1. A method for rapid detection of one or a multiplicity of cells comprising the steps of:
    filtrating a sample comprising one or a multiplicity of cells through one or a multiplicity of micro-channels that are positioned adjacent to and above a filter so as to trap the one or multiplicity of cells with the one or a multiplicity of micro-channels, and wherein the one or multiplicity of micro-channels have a volume of about 1-500 picoliters, and wherein the ratio of the diameter to a length of the one or a multiplicity of micro-channels is between about 1:10 to 1:100,
    growing the one or a multiplicity of cells inside the one or a multiplicity of microchannels into one or a multiplicity of micro-colonies, and
    detecting the one or multiplicity of micro-colonies.

2. The method of claim 1, wherein the filter is porous such that the pores are smaller than an average of a size of the one or a multiplicity of cells.

3. The method of claim 1, wherein the filtrating step includes removing effluent that passes through the one or a multiplicity of micro-channels with a manifold.

4. The method of claim 1, wherein the filtrating of the sample is aided with a pump.

5. The method of claim 1, wherein the filtrating step further includes filtering the sample through a porous support, the porous support adjacent the filter opposite the one or a multiplicity of micro-channels.

6. The method of claim 1, wherein the filtration step further includes adding the sample into a funnel, wherein the funnel directs the sample into the one or a multiplicity of micro-channels.

7. The method of claim 1, wherein the filtration step includes adding the sample to the one or a multiplicity of micro-channels in the substantial absence of ambient air pressure.

8. The method of claim 7, wherein the substantial absence of ambient air pressure is achieved by mounting a syringe to a top side of the one or a multiplicity of micro-channels.

9. The method of claim 1, wherein the sample is selected from the group consisting of liquids and bioaerosols.

10. The method of claim 1, wherein the micro-channels are substantially cylindrical.

11. The method of claim 1, wherein the micro-colonies obtain cylindrical shape within the one or a multiplicity of micro-channels.

12. The method of claim 1, wherein the growing step includes placing the one or a multiplicity of micro-channels and the filter on a nutrient media, the nutrient media adjacent to the filter opposite the micro-channels.

13. The method of claim 12, wherein the filter and one or a multiplicity of micro-channels is removed from the nutrient media and an indicator is introduced to the micro-colonies by placing the one or a multiplicity of micro-channels and the filter on a surface containing the indicator, the surface adjacent the filter opposite the one or a multiplicity of micro-channels.

14. The method of claim 12, wherein the nutrient media is selected from the group consisting of solid nutrient media or liquid nutrient media.

15. The method of claim 1, wherein the number of the one or a multiplicity of cells in the sample is equal or less than 50% of the number of the multiplicity of micro-channels.

16. The method of claim 15, wherein the number of the one or a multiplicity of cells in the sample is equal or less than 15% of the number of the multiplicity of micro-channels.

17. The method of claim 1, further comprising the step of introducing an indicator to the micro-colonies subsequent to the growing step.

18. The method of claim 17, wherein the indicator is introduced to the microcolonies by placing the one or a multiplicity of micro-channels and the filter on a surface containing the indicator, the surface adjacent the filter opposite the one or a multiplicity of micro-channels.

19. A method for cylindrically shaping one or a multiplicity of micro-colonies to create rapid detection of the one or a multiplicity of colonies, comprising the steps of:

introducing one or a multiplicity of cells into one or a multiplicity of substantially cylindrical micro-channels, wherein the substantially cylindrical micro-channels have a volume of about 1-500 picoliters, and wherein the ratio of the diameter to a length of the one or a multiplicity of micro-channels is between about 1:10 to 1:100 growing the one or a multiplicity of cells into the one or a multiplicity of microcolonies, such that the one or a multiplicity of micro-colonies have a substantially cylindrical shape inside the one or a multiplicity of substantially cylindrical microchannels, and detecting visually the one or a multiplicity of micro-colonies.

20. The method of claim 19, wherein the step of visually detecting the one or multiplicity of micro-colonies utilizes an indicator selected from the group consisting of: chromogenic substrates or absorbent dyes; fluorogenic substrate or fluorescent dyes; Tetrazolium salts; iron sulfide or potassium telluride in agar; and pH indicators for detecting microcolonies with changed pH.

* * * * *